(12) United States Patent
Heal et al.

(10) Patent No.: US 6,403,641 B2
(45) Date of Patent: *Jun. 11, 2002

(54) THERAPEUTIC AGENTS

(75) Inventors: David John Heal; Helen Christine Jackson, both of Nottingham (GB)

(73) Assignee: Abbott Labortories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/212,249

(22) Filed: Dec. 16, 1998

(30) Foreign Application Priority Data

Dec. 24, 1997 (GB) .............................. 9727131

(51) Int. Cl.⁷ .............................. A61K 31/30
(52) U.S. Cl. ...................................... 514/499
(58) Field of Search ......................... 314/499

(56) References Cited

U.S. PATENT DOCUMENTS

| | | | |
|---|---|---|---|
| 4,598,089 A | * 7/1986 | Hadvary et al. | 514/449 |
| 4,939,175 A | 7/1990 | Ukai et al. | 514/646 |
| 4,983,746 A | 1/1991 | Barbier et al. | 549/328 |
| 5,643,874 A | 7/1997 | Bremer et al. | 514/12 |

FOREIGN PATENT DOCUMENTS

| | | |
|---|---|---|
| EP | 230742 | 8/1987 |
| EP | 397831 | 9/1993 |
| GB | 2098602 | 11/1982 |
| WO | 88/06444 | 9/1988 |
| WO | 95/20949 | 8/1995 |

OTHER PUBLICATIONS

Buttle, Expert Opinion on Investigational Drugs, 5(12):1583–1587, 1996.*
Stricker–Krongrad et al., Int. J. Obesity, 19, p. 145, P399, 1995.*
Connolly et al., "Valvular Heart Disease Associated with Fenfluramine–Phentermine", The New England Journal of Medicine, vol. 337, No. 9, pp. 581–588, Aug. 28, 1997.*
Buckett et al., Prog. Neuro–Phys. & Biol. Psych., 1988, vol. 12, 575–584.
Fantino et al., Int. J. Obesity, 19, p.145, 1995.
Stricker–Krongrad et al., Int. J. Obesity, 19, p. 145, P399, 1995.
Halford et al., Brit. J. Pharm., 114, 387P, 1995.
Connoley et al, Brit. J. Pharm, 114, 388P, 1995.
Connoley et al., Brit. J. Pharm, 170P, 1996.
Borgstrom, Biochimica et Biophysica Acta, 962, 1988, pp. 308–316.
Buttle, Expert Opinion on Investigational Drugs, 5/12 (1583–1587, XP002105328, 1996.
Wilding, British Medical Bull., V315, Oct. 18, 1997, 997–1000.
Finer, British Medical Bull., 53/2, 409–432, 1997.
New York Times, May 15, 1997.
Parker, Scrip Reports, "Obesity Trends and Treatments", Oct. 1996, pp. 21–33.

* cited by examiner

Primary Examiner—Dwayne C. Jones
(74) Attorney, Agent, or Firm—Keil & Weinkauf

(57) ABSTRACT

A method for the treatment of obesity in a human in need of such treatment which comprises administration to the human of a therapeutically effective amount of a compound of formula I

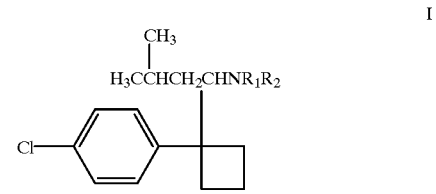

including enantiomers and pharmaceutically acceptable salts thereof, in which $R_1$ and $R_2$ are independently H or methyl, and a therapeutically effective amount of a compound of formula II

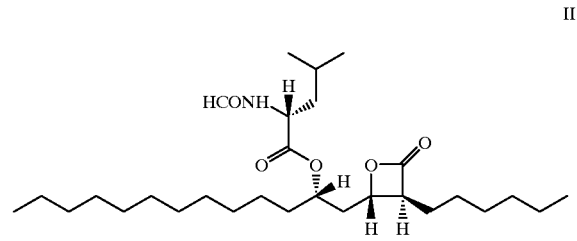

wherein the compound of formula I and the compound of formula II are administered simultaneously, separately or sequentially.

9 Claims, No Drawings

THERAPEUTIC AGENTS

BACKGROUND OF THE INVENTION

This invention relates to a method for treating obesity and to products and pharmaceutical compositions suitable for use in such a method. More particularly, the invention relates to a method for the treatment of obesity by the administration of sibutramine or a salt or a metabolite thereof and; orlistat and to products and compositions containing such compounds.

Sibutramine hydrochloride monohydrate and orlistat are both currently being developed for use in the treatment of obesity. The two compounds, however, achieve weight loss through entirely different mechanisms.

Sibutramine is a 5-hydroxytryptamine and noradrenaline reuptake inhibitor in vivo (Buckett, W. R., Thomas, P. C. & Luscombe, G. P. (1988). Prog. Neuro-Psychopharmacol. Biol. Psychiat. 12, 575–584 and Luscombe, G. P., Hopcroft, R. H., Thomas, P. C. & Buckett, W. R. (1989). Neuropharmacology, 28, 129–134.) Studies have shown that it reduces body weight by a dual mode of action; it decreases food intake by enhancing satiety (Fantino, M. & Souquet, A. -M. (1995). Int. J. Obesity, 19, 145; Halford, J. C. G., Heal, D. J. & Blundell, J. E. (1995). Brit. J. Pharmacol. 114, 387P; and Stricker-Krongrad, A., Souquet, A. -M. & Burlet, C. (1995). Int. J. Obesity, 19, 145.), and it increases energy expenditure by stimulating thermogenesis (Connoley, I. P., Heal, D. J. & Stock, M. J. (1995). Brit. J. Pharmacol. 114, 388P; and Connoley, I. P., Frost, I., Heal, D. J. & Stock, M. J. (1996). Brit. J. Pharmacol. 117, 170P).

Orlistat inhibits lipase enzymes which are responsible for breaking down ingested fat (Borgstrom, B. (1988). Biochem. Biophys. Acta. 962 (3), 308–316); as a consequence of this, unabsorbed fat is egested in the faeces, It has been reported that orlistat should not be combined with appetite suppressants ( The New York Times May 15, 1997). Surprisingly, it has now been found that co-administration of sibutramine hydrochloride monohydrate and orlistat results in beneficial effects with respect to weight-loss.

Accordingly, the present invention provides a method for the treatment of obesity in a human in need of such treatment which comprises administration to the human of a therapeutically effective amount of a compound of formula I

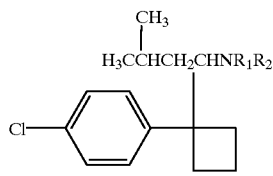

I including enantiomers and pharmaceutically acceptable salts thereof, in which $R_1$ and $R_2$ are independently H or methyl, and a therapeutically effective amount of a compound of formula II

II

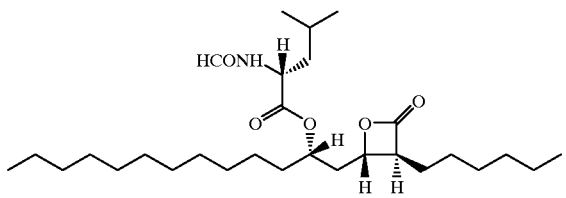

wherein the compound of formula I and the compound of formula II are administered simultaneously, separately or sequentially.

The present invention may provide the following advantages. Firstly, the maximum weight loss achieved is greater than that achieved by the sole administration of either a compound of formula I or compound II. Secondly, a synergistic weight loss is achieved in which the weight loss obtained by the administration of a compound of formula I and the compound of formula II to a first test group is greater than the total weight loss achieved by administration of the compound of formula I to a second test group and the weight loss achieved by administration of compound II to a third test group. Thirdly, when weight loss has reached a plateau after administration of either a compound of formula I or the compound II, a further weight loss is achieved by administering the other compound. Fourthly, lower doses of the compound of formula I and the compound of formula II may be used in the present invention thus reducing the side-effects associated with administration of a higher dose of each compound.

A preferred compound of formula I is N-{1-[1-(4-chlorophenyl)cyclobutyl]-3-methylbutyl}-N,N-dimethylamine or a salt thereof, for example the hydrochloride salt, known as sibutramine hydrochloride. A preferred form of this hydrochloride is its monohydrate, known as sibutramine hydrochloride monohydrate.

The preparation and use of compounds of formula I, such as N-{1-[1-(4-chlorophenyl)cyclobutyl]-3-methylbutyl}-N,N-dimethylamine and salts thereof, in the treatment of depression is described in British Patent Specification 2098602. The use of compounds of formula I such as N-{1-[1-(4-chlorophenyl)cyclobutyl]-3-methylbutyl}-N,N-dimethylamine and salts thereof in the treatment of Parkinson's disease is described in published PCT application WO 88/06444. The use of N-{1-[1-(4-chlorophenyl)cyclobutyl]-3-methylbutyl}-N,N-dimethylamine and salts thereof in the treatment of cerebral function disorders is described in U.S. Pat. No. 4,939,175. The use of N-{1-[1-(4-chlorophenyl)cyclobutyl]-3-methylbutyl}-N,N-dimethylamine hydrochloride in the treatment of obesity is described in European Patent Number 397831. A particularly preferred form of this compound is N-{1-[1-(4-chlorophenyl)cyclobutyl]-3-methylbutyl}-N,N-dimethylamine hydrochloride monohydrate (sibutramine hydrochloride monohydrate) which is described in European Patent Number 230742. The use of N-{1-[1-(4-chlorophenyl)cyclobutyl]-3-methylbutyl}-N,N-dimethylamine and salts thereof for improving the glucose tolerance of humans having Impaired Glucose Tolerance or Non-Insulin Dependent Diabetes Mellitus is described in published PCT application WO95/20949.

The compound of formula II has the chemical name (2S, 3S, 5S)-5-[(S)-2-formamido-4-methylvaleryloxy]-2-hexyl-3-hydroxyhexadecanoic acid lactone. It is also known as "N-formyl-L-leucine, ester with (3S, 4S)-3-hexyl4-[(2S)-2-hydroxy-tridecyl]-2-oxetanone", (−)-tetrahydrolipstatin, tetrahydrolipistatin, and orlistat.

The extraction and use of orlistat in the control or prevention of obesity and hyperlipaemia is described in U.S. Pat. No. 4598089 (Hoffmann-La Roche Inc.). A process for the preparation of orlistat is described in U.S. Pat. No. 4983746 (Hoffmann-La Roche Inc.). A composition comprising orlistat and acarbose is described in EP638317 (Hoffmann-La Roche AGF).

It will be appreciated by those skilled in the art that compounds of formula I contain a chiral center. When a compound of formula I contains a single chiral center it may exist in two enantiomeric forms. The present invention includes the use of the individual enantiomers and mixtures of the enantiomers. The enantiomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer to the other by asymmetric transformation. Enantiomers of secondary and tertiary amines of formula I can also be prepared by preparing the primary amine racemate, resolving this mixture into its individual enantiomers and then converting the relevant optically pure primary amine enantiomer into the desired secondary or tertiary amine product.

Preferred compounds of formula I are N-{1-[1-(4-chlorophenyl)cyclobutyl]-3-methylbutyl}-N,N-dimethylamine, N-{1-[1-(4-chlorophenyl)cyclobutyl]-3-methylbutyl}-N-methylamine, and N-1-[1-(4-chlorophenyl)cyclobutyl]-3-methylbutylamine including racemates, individual enantiomers and mixtures thereof, and pharmaceutically acceptable salts thereof. Specific enantiomers of formula I are (+) -N-{1-[1-(4-chlorophenyl)cyclobutyl]-3-methylbutyl}-N,N-dimethylamine, (−)-N-{1-[1-(4-chlorophenyl) cyclobutyl]-3-methylbutyl}-N,N-dimethylamine, (R)-(+)-N-{1-[1-(4-chlorophenyl) cyclobutyl]-3-methylbutyl}-N-methylamine, (S)-(−)-N{1-[1-(4-chlorophenyl)cyclobutyl]-3-methylbutyl}-N-methylamine, (R)-(+)-1-[1-(4 -chloro-phenyl)cyclobutyl]-3-methylbutylamine and (S)-(−)-1-[1-(4-chlorophenyl) cyclobutyl]-3-methylbutylamine.

In the method of the present invention a compound of formula I and the compound of formula II may be administered concomitantly or concurrently, for example in the form of separate dosage units to be used simultaneously, separately or sequentially.

In another aspect the present invention provides a compound of formula I including enantiomers and pharmaceutically acceptable salts thereof, in which R₁ and R₂ are independently H or methyl and the compound of formula II for simultaneous, separate or sequential use for the treatment of obesity.

In yet another aspect the present invention provides a compound of formula I including enantiomers and pharmaceutically acceptable salts thereof, in which $R_1$ and $R_2$ are independently H or methyl and the compound of formula II as a combined preparation for simultaneous, separate or sequential use for the treatment of obesity.

In a further aspect the present invention provides a product containing a compound of formula I including enantiomers and pharmaceutically acceptable salts thereof, in which $R_1$ and $R_2$ are independently H or methyl and the compound of formula II as a combined preparation for simultaneous, separate or sequential use for the treatment of obesity.

In yet another aspect the present invention provides the use of a compound of formula I including enantiomers and pharmaceutically acceptable salts thereof, in which $R_1$ and $R_2$ are independently H or methyl in the manufacture of a medicament for the treatment of obesity in a patient who is also receiving treatment with orlistat.

In a further aspect, the present invention provides a method of treating obesity comprising the administration of an adjunctive therapy comprising a therapeutically effective amount of a compound of formula I and orlistat to a patient in need thereof.

The invention also provides the use of the above combination of drugs in the manufacture of a medicament for the treatment of obesity. Additionally, it provides the combination for use in the treatment of obesity.

The amount of each compound to be administered will depend on a number of factors including the age of the patient, the severity of the condition and the past medical history of the patient and always lies within the sound discretion of the administering physician but it is generally envisaged that the dosage of the compound of formula I to be administered will be in the range 0.1 to 50 mg preferably 1 to 30 mg per day given in one or more doses and more preferably 10 mg, 15 mg, 20 mg, 25 mg or 30 mg per day and most preferably 20 mg. The dosage of orlistat to be administered will be in the range of 50 to 1440 mg given in one or more doses, preferably three times daily, more preferably in the range of 120 to 720 mg and most preferably in the range of 120 to 360 mg. The compound of formula I, preferably sibutramine hydrochloride monohydrate, may be administered in any of the known pharmaceutical dosage forms. Orlistat is preferably administered orally.

In a preferred aspect of the present invention sibutramine hydrochloride monohydrate is administered once daily, preferably first thing in the morning, and orlistat is administered three times daily either with or before meals. Preferably the dose of sibutramine hydrochloride monohydrate is 20 mg or 30 mg administered once daily and the dose of orlistat is 120 mg administered three times daily either with or before meals. Most preferably the dose of sibutramine hydrochloride monohydrate is given prior to the first dose of orlistat, preferably in the range of 30 minutes to 3 hours, for example 30 minutes, 1 hour, 1.5 hours, 2 hours, 2.5 hours or 3 hours, before the first dose orlistat.

In another aspect of to the present invention there is provided a pharmaceutical composition comprising a compound of formula I

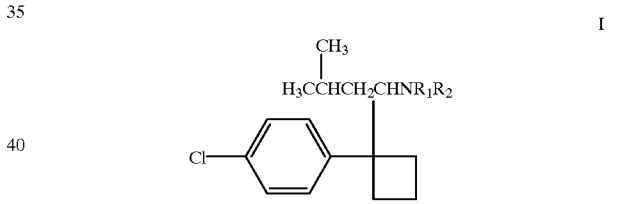

including enantiomers and pharmaceutically acceptable salts thereof, in which $R_1$ and $R_2$ are independently H or methyl, and the compound of formula II

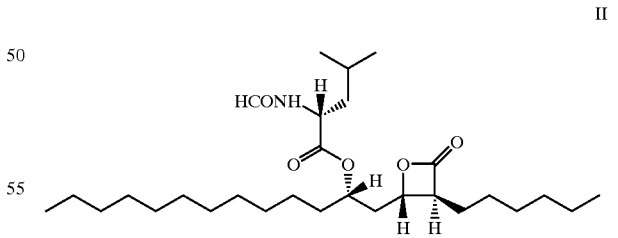

in conjunction with a pharmaceutically acceptable diluent or carrier.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacist's art. Tablets may be prepared from a mixture of the active compounds with fillers, for example calcium phosphate; disintegrating agents, for example maize starch; lubricating agents, for example magnesium stearate; binders, for example microcrystalline cellulose or polyvinylpyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 1 to 50 mg of the compound of formula I and 1 to 360 mg of orlistat.

Other dosage forms for oral administration include, for example, aqueous suspensions containing the active compounds in an aqueous medium in the presence of a non-toxic suspending agent such as sodium carboxy-methylcellulose, and oily suspensions containing the active compounds in a suitable vegetable oil, for example arachis oil. The active compounds may be formulated into granules with or without additional excipients. The granules may be ingested directly by the patient or they may be added to a suitable liquid carrier (for example, water) before ingestion. The granules may contain disintegrants, eg an effervescent couple formed from an acid and a carbonate or bicarbonate salt to facilitate dispersion in the liquid medium.

The compounds of formula I and orlistat may be formulated into a composition which the patient retains in his mouth so that the active compounds are administered through the mucosa of the mouth.

Dosage forms of the compounds of formula I suitable for rectaladministration are the known pharmaceutical forms for such administration, for example, suppositories with cocoa butter or polyethylene glycol bases.

Dosage forms of the compounds of formula I suitable for parenteral administration are the known pharmaceutical forms for such administration, for example sterile suspensions or sterile solutions in a suitable solvent.

Dosage forms of the compounds of formula I for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream, gel or ointment base. The amount of each active compound contained in a topical formulation should be such that a therapeutically effective amount of each compound is delivered during the period of time for which the topical formulation is intended to be on the skin.

The compounds of formula I may be formulated into a composition which is dispersed as an aerosol into the patients oral or nasal cavity. Such aerosols may be administered from a pump pack or from a pressurised pack containing a volatile propellant.

The compound of formula I may also be administered by continuous infusion either from an external source, for example by intravenous infusion or from a source of the compound placed within the body. Internal sources include implanted reservoirs containing the compounds to be infused which is continuously released for example by osmosis and implants which may be (a) liquid such as an oily suspension of the compounds to be infused for example in the form of a very sparingly water-soluble derivative such as a dodecanoate salt or a lipophilic ester or (b) solid in the form of an implanted support, for example of a synthetic resin or waxy material, for the compounds to be infused. The support may be a single body containing all the compounds or a series of several bodies each containing part of the compounds to be delivered. The amount of active compounds present in an internal source should be such that a therapeutically effective amount of each compound is delivered over a long period of time.

In some formulations it may be beneficial to use the compounds of the present invention in the form of particles of very small size, for example as obtained by fluid energy milling.

In the compositions of the present invention the active compounds may, if desired, be associated with other compatible pharmacologically active ingredients. Optionally vitamin supplements may be administered with the compounds of the present invention.

Pharmaceutical compositions incorporating both a compound of formula I and orlistat are important embodiments of the present invention. Such pharmaceutical compositions contain a therapeutically effective amount of each of the compounds. Each dosage unit may contain the daily doses of both compounds, or may contain a fraction of the daily dose, such as one-third of the doses. Alternatively, each dosage unit may contain the entire dose of one of the compounds, and a fraction of the dose of the other compound. In such case, the patient would daily take one of the combination dosage units, and one or more units containing only the other compound.

The use of compounds of the present invention in the manufacture of pharmaceutical compositions is illustrated by the following description. In this description the term "active compound" denotes either or both compounds of the invention unless otherwise stated.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

Tablets

Tablets are prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories (Compound of Formula I only)

In the preparation of suppositories, 100 parts by weight of active compound is incorporated in 1300 parts by weight of triglyceride suppository base and the mixture formed into suppositories each containing a therapeutically effective amount of active ingredient.

Formulation 1
Hard gelatin capsules are prepared using the following ingredients:

| | Quantity (mg/capsule) |
|---|---|
| Sibutramine hydrochloride monohydrate | 20 |
| Orlistat | 120 |
| Starch | 200 |
| Magnesium stearate | 10 |
| Total | 350 |

Formulation 2
A tablet is prepared using the ingredients below:

| | Quantity (mg/tablet) |
|---|---|
| Sibutramine hydrochloride monohydrate | 10 |
| Orlistat | 120 |
| Microcrystalline Cellulose | 400 |
| Silica | 10 |
| Stearic acid | 5 |
| Total | 545 |

The components are blended and compressed to form tablets each weighing 545 mg.

The advantages of the present invention may be demonstrated by one or more of the following studies Study 1

Groups of normal adult male Sprague-Dawley CD rats (n=8–12) receive the following treatments
- a) Group 1; daily dosing with sibutramine hydrochloride monohydrate (1, 3 or 10 mg/kg po) plus orlistat vehicle po.
- b) Group 2; bidaily dosing of orlistat po (for example 10, 20, 30 or 40 mg/kg po preferably 10 or 20 mg/kg) plus sibutramine vehicle po.
- c) Group 3; combined po treatment with doses of sibutramine hydrochloride monohydrate and orlistat.
- d) Group 4; control, dosed po with sibutramine and orlistat vehicles.

The rats are allowed free access to high-fat diet. Food intake, water intake and body-weight are measured daily and the duration of treatment is 15, 21 or 28 days. A statistical comparison between the body weights of the animals in each group provides results demonstrating the advantage of the present invention.

Study 2

Groups of obese female Zucker rats (n=8–12) maintained on a high-fat diet receive the following treatments
- a) Group 1; daily po dosing with sibutramine hydrochloride monohydrate for 14 days at a dose which significantly reduces body weight compared to vehicle-treated controls (1, 3 or 10 mg/kg po). Daily treatment for the next 14 days is with an identical dose of sibutramine hydrochloride monohydrate po plus a dose of orlistat (for example 10, 20, 30 or 40 mg/kg po preferably 10 or 20 mg/kg).
- b) Group 2; daily dosing with sibutramine hydrochloride monohydrate po for 14 days. Daily treatment for the next 14 days with sibutramine po and orlistat vehicle po.
- c) Group 3; daily dosing with sibutramine hydrochloride monohydrate vehicle po for 14 days followed by combined treatment with sibutramine hydrochloride monohydrate vehicle po and orlistat vehicle po for the following 14 days.

A statistical comparison between the body weights of animals in each group provides results demonstrating the advantage of the present invention.

What is claimed is:

1. A method for treatment of obesity in a human in need of such treatment which comprises administration to the human of a therapeutically effective amount of a compound of formula I

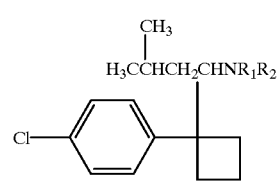

and its enantiomers and pharmaceutically acceptable salts thereof, in which $R_1$ and $R_2$ are independently H or methyl, and the compound of formula II

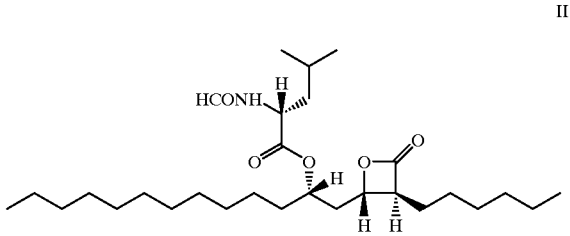

wherein the compound of the formula I and the compound of formula II are administered simultaneously, separately or sequentially.

2. A method according to claim 1 in which the compound of formula I is $\underline{N}$-{1-[1-(4-chlorophenyl)cyclobutyl]-3-methylbutyl}-$\underline{N},\underline{N}$-dimethylamine or a salt thereof.

3. A method according to claim 2 wherein the compound of formula I is administered 30 minutes to 3 hours prior to the administration of the compound of formula II.

4. A product containing a compound of formula I

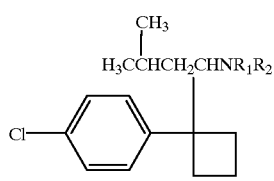

I and its enantiomers and pharmaceutically acceptable salts thereof, in which $R_1$ and $R_2$ are independently H or methyl and the compound of formula II

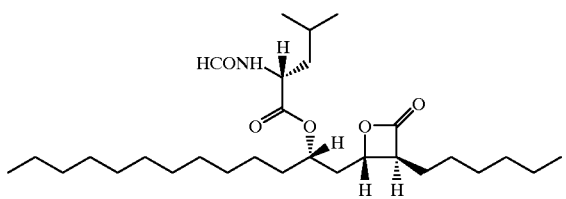

II as a combined preparation for simultaneous, separate or sequential use for the treatment of obesity.

5. A pharmaceutical composition comprising a compound of formula I

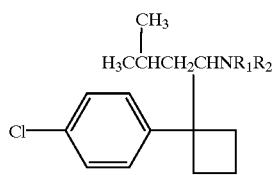

I and its enantiomers and pharmaceutically acceptable salts thereof, in which $R_1$ and $R_2$ are independently H or methyl, and the compound of formula II

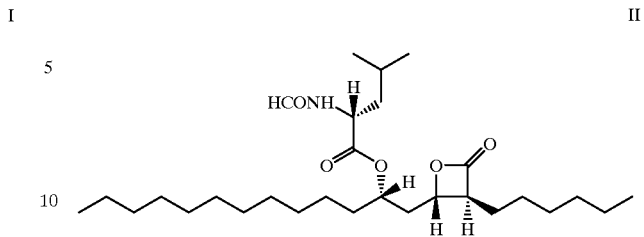

II in conjunction with a pharmaceutically acceptable diluent or carrier.

6. A method according to claim 3 wherein the compound of formula I is sibutramine hydrochloride monohydrate and is administered once daily in a dose of 20 mg or 30 mg.

7. A method according to claim 6 wherein the compound of formula II is orlistat and is administered three times daily either with or before meals in a dose of 120 mg.

8. A method according to claim 7, wherein the compound of formula I is administered first thing in the morning and the first dose of the compound of formula II is administered from 30 minutes to 3 hours later.

9. A method according to claim 1, wherein the compound of the formula I and the compound of the formula II are administered orally.

* * * * *